(12) United States Patent
Walls et al.

(10) Patent No.: US 8,338,657 B1
(45) Date of Patent: Dec. 25, 2012

(54) MEDICAL DRESSING

(76) Inventors: Charlene P. Walls, Charlotte, NC (US);
Jeffrey J. Schwartz, Matthews, NC (US)

( * ) Notice: Subject to any disclaimer, the term of this patent is extended or adjusted under 35 U.S.C. 154(b) by 739 days.

(21) Appl. No.: 12/156,510

(22) Filed: Jun. 2, 2008

Related U.S. Application Data

(60) Provisional application No. 60/941,560, filed on Jun. 1, 2007.

(51) Int. Cl.
*A61F 13/00* (2006.01)

(52) U.S. Cl. .......................... 602/43; 604/304

(58) Field of Classification Search .......... 602/13, 602/79, 42–53; 128/889, 890; 604/304–309; 606/213
See application file for complete search history.

(56) References Cited

U.S. PATENT DOCUMENTS

| | | | | |
|---|---|---|---|---|
| 3,117,573 | A * | 1/1964 | Snell | 128/837 |
| 3,194,235 | A | 7/1965 | Cooke | |
| 3,782,377 | A | 1/1974 | Rychlik | |
| 5,003,971 | A * | 4/1991 | Buckley | 602/54 |
| 5,018,534 | A | 5/1991 | Grant | |
| 5,074,847 | A | 12/1991 | Greenwell et al. | |
| 5,181,274 | A | 1/1993 | De Fiore | |
| D335,926 | S | 5/1993 | Rozier et al. | |
| 5,263,922 | A * | 11/1993 | Sova et al. | 602/59 |
| 5,580,346 | A * | 12/1996 | Spier | 602/42 |
| 5,758,660 | A * | 6/1998 | Lokken | 128/877 |
| 6,987,209 | B2 * | 1/2006 | Augustine et al. | 602/42 |
| 7,205,449 | B2 * | 4/2007 | Levin | 602/58 |
| 2003/0139696 | A1 * | 7/2003 | Boukanov et al. | 602/41 |
| 2008/0234616 | A1 * | 9/2008 | Shives et al. | 602/13 |

OTHER PUBLICATIONS

D.G. Maki and M. Ringer, JAMA The Journal of the American Medical Association, "Evaluation of Dressing regimens for prevention of infection with peripheral intravenous catheters. Gauze, a transparent polyurethane dressing, and an iodophor-transparent dressing", http://jama.ama-assn.org/cgi/content/abstract/258/17/2396; vol. 258 No. 17, Nov. 6, 1987; pp. 1-3.

* cited by examiner

*Primary Examiner* — Loan Thanh
*Assistant Examiner* — Tarla Patel
(74) *Attorney, Agent, or Firm* — Schwartz Law Firm, P.C.

(57) ABSTRACT

A medical dressing for an open wound includes a base, and a raised flexible therapeutic cover formed with base. The base has opposing inside and outside major surfaces, and continuous inside and outside peripheral edges. The inside peripheral edge defines a wound site opening and designed to surround the open wound. The raised-flexible therapeutic cover extends over and above the wound site opening defined by the inside peripheral edge. A compression spring resiliently spaces the therapeutic cover from the open wound.

17 Claims, 6 Drawing Sheets

MEDICAL DRESSING

TECHNICAL FIELD AND BACKGROUND

The present disclosure relates broadly and generally to the medical field, and more particularly to disposable medical wound dressings. According to medical research and various published articles, an "ideal" wound dressing is one that is sterile, breathable, and encourages a moist healing environment. Such conditions generally reduce the risk of infection, help the wound heal more quickly, and reduce scarring.

SUMMARY OF EXEMPLARY EMBODIMENTS

Various exemplary embodiments of the present invention are described below. Use of the term "exemplary" means illustrative or by way of example only, and any reference herein to "the invention" is not intended to restrict or limit the invention to exact features or steps of any one or more of the exemplary embodiments disclosed in the present specification. References to "exemplary embodiment," "one embodiment," "an embodiment," "various embodiments," and the like, may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

According to one exemplary embodiment, a medical dressing for an open wound includes a base, and a raised flexible therapeutic cover formed with base. The base has opposing inside and outside major surfaces, and continuous inside and outside peripheral edges. The inside peripheral edge defines a wound site opening and designed to surround the open wound. The raised flexible therapeutic cover extends over and above the wound site opening defined by the inside peripheral edge. Means are provided for resiliently spacing the therapeutic cover from the open wound.

The term "open wound" is used broadly herein to mean a type of injury or condition in which the skin is torn, cut, or punctured.

According to another exemplary embodiment, the means comprises a compression spring integrally formed with the therapeutic cover. The term "compression spring" refers broadly herein to any type of spring designed to compress and become smaller when presented with compressive load.

According to another exemplary embodiment, the compression spring comprises a helical coil spring.

According to another exemplary embodiment, the therapeutic cover incorporates a see-through wound site window.

According to another exemplary embodiment, the wound site window incorporates a transparent film.

According to another exemplary embodiment, the therapeutic cover incorporates a perforated flexible gauze.

According to another exemplary embodiment, an adhesive label is releasably adhered to the outside major surface of the base.

According to another exemplary embodiment, the outside major surface of the base includes a poly-coating between the base and the adhesive label.

According to another exemplary embodiment, the inside major surface of the base includes an adhesive coating adapted for temporarily adhering the medical dressing to skin surrounding the open wound.

According to another exemplary embodiment, a protective poly-coated release paper is provided adjacent the adhesive coating of the base.

In yet another exemplary embodiment, the medical dressing includes a base comprising an annular flange, and a raised flexible therapeutic cover formed with the flange. The annular flange has opposing inside and outside major surfaces, and continuous inside and outside peripheral edges. The inside peripheral edge defines a wound site opening, and is designed to encircle the open wound. The raised flexible therapeutic cover extends over and above the wound site opening defined by the inside peripheral edge. Means are provided for resiliently spacing the therapeutic cover from the open wound.

According to another exemplary embodiment, first and second substantially semi-circular adhesive labels are releasably adhered to the outside major surface of the annular flange.

BRIEF DESCRIPTION OF THE DRAWINGS

The description of exemplary embodiments proceeds in conjunction with the following drawings, in which.

DESCRIPTION OF EXEMPLARY EMBODIMENTS AND BEST MODE

The present invention is described more fully hereinafter with reference to the accompanying drawings, in which one or more exemplary embodiments of the invention are shown. Like numbers used herein refer to like elements throughout. This invention may, however, be embodied in many different forms and should not be construed as limited to the embodiments set forth herein; rather, these embodiments are provided so that this disclosure will be operative, enabling, and complete. Accordingly, the particular arrangements disclosed are meant to be illustrative only and not limiting as to the scope of the invention, which is to be given the full breadth of the appended claims and any and all equivalents thereof. Moreover, many embodiments, such as adaptations, variations, modifications, and equivalent arrangements, will be implicitly disclosed by the embodiments described herein and fall within the scope of the present invention.

Although specific terms are employed herein, they are used in a generic and descriptive sense only and not for purposes of limitation. Unless otherwise expressly defined herein, such terms are intended to be given their broad ordinary and customary meaning not inconsistent with that applicable in the relevant industry and without restriction to any specific embodiment hereinafter described. As used herein, the article "a" is intended to include one or more items. Where only one item is intended, the term "one", "single", or similar language is used. When used herein to join a list of items, the term "or" denotes at least one of the items, but does not exclude a plurality of items of the list.

For exemplary methods or processes of the invention, the sequence and/or arrangement of steps described herein are illustrative and not restrictive. Accordingly, it should be understood that, although steps of various processes or methods may be shown and described as being in a sequence or temporal arrangement, the steps of any such processes or methods are not limited to being carried out in any particular sequence or arrangement, absent an indication otherwise. Indeed, the steps in such processes or methods generally may be carried out in various different sequences and arrangements while still falling within the scope of the present invention.

Additionally, any references to advantages, benefits, unexpected results, or operability of the present invention are not intended as an affirmation that the invention has been previously reduced to practice or that any testing has been performed. Likewise, unless stated otherwise, use of verbs in the past tense (present perfect or preterite) is not intended to indicate or imply that the invention has been previously reduced to practice or that any testing has been performed.

Figure 1:
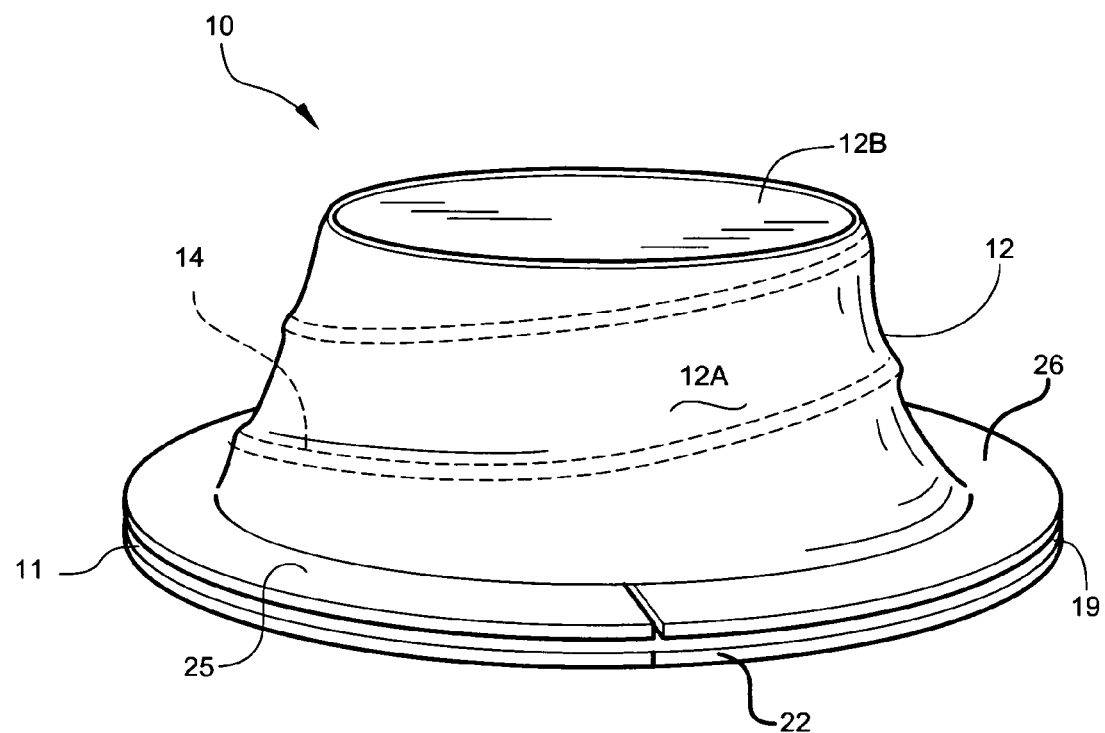
FIG. 1 is a perspective view of a medical dressing according to one exemplary embodiment of the present disclosure.
Figure 2:
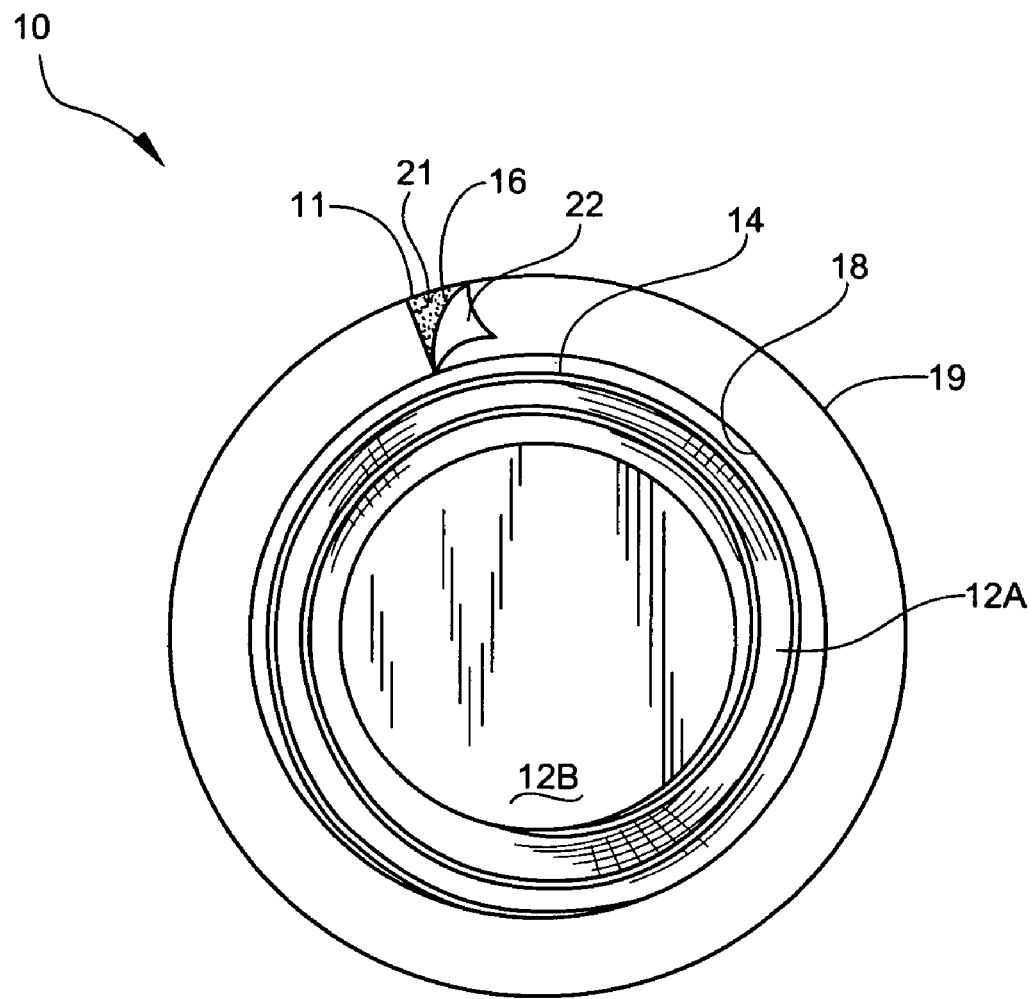
FIG. 2 is bottom side view of the medical dressing.
Figure 3:
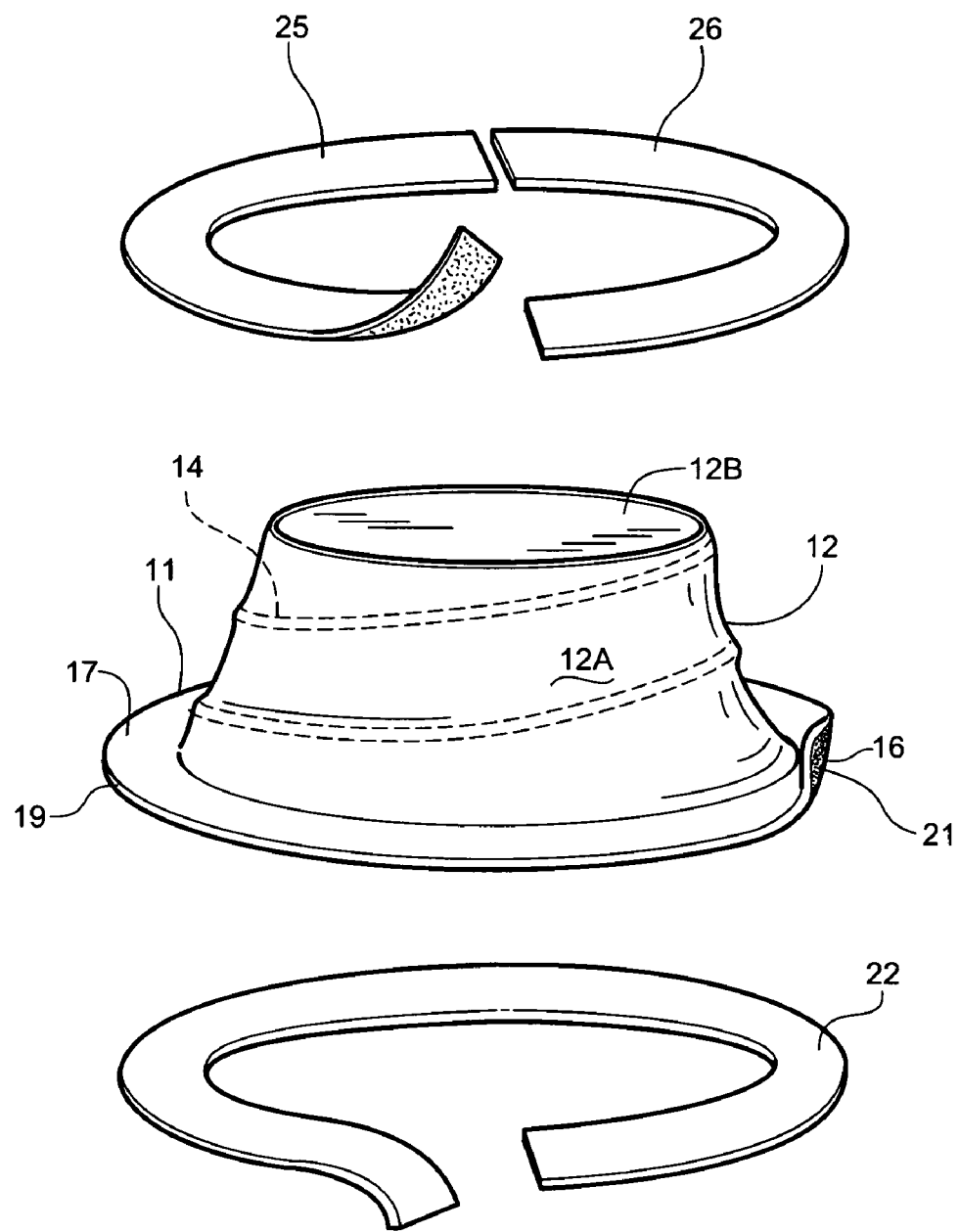
FIG. 3 is a perspective view of the medical dressing, and showing various releasable elements exploded away.

Referring now specifically to the drawings, a medical dressing according to one exemplary embodiment of the present invention is illustrated in FIG. 1 and shown generally at reference numeral 10. The medical dressing 10 is especially applicable for protecting and/or treating any open wound on a patient, including (e.g.) skin punctures for IV catheters, cuts, scraps, tears, abrasions, and other skin conditions. In the exemplary embodiment shown, the medical dressing 10 includes an annular base 11, a raised flexible therapeutic cover 12 formed with the base 11, and a compression spring 14 integrally formed with the cover 12. As shown in FIGS. 1, 2, and 3, the base 11 may comprise an annular flange having opposing inside and outside major surfaces 16 and 17, and continuous inside and outside peripheral edges 18 and 19. The inside peripheral edge 18 defines an annular wound site opening, and is adapted to substantially surround (or encircle) the open wound. In alternative embodiments, the base, including its inside and outside peripheral edges, may be formed in any other desired size, shape, and/or configuration.

Figure 4:
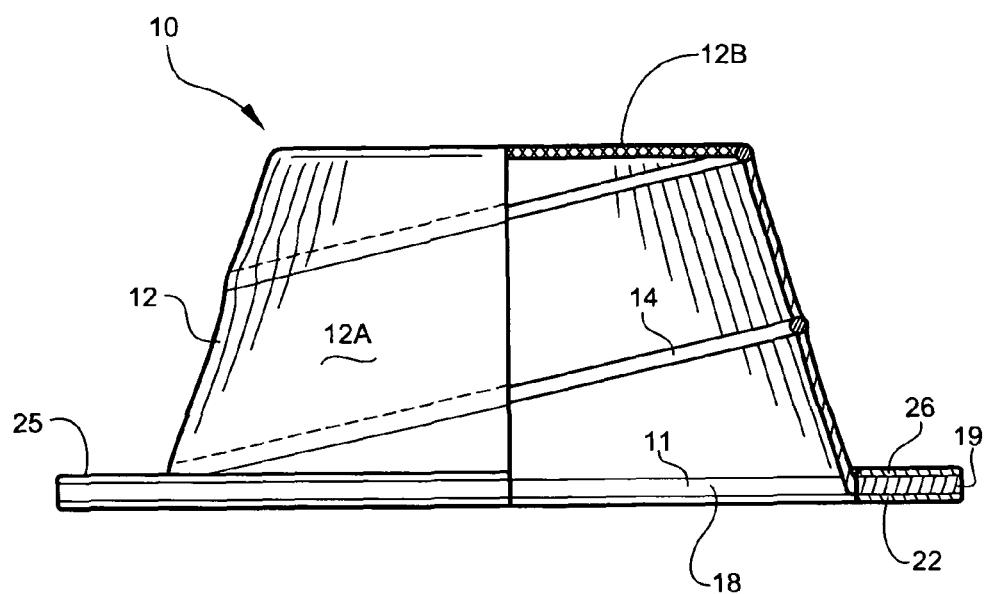
FIG. 4 is a partial cross-section of the medical dressing with the therapeutic cover in an extended condition.
Figure 5:
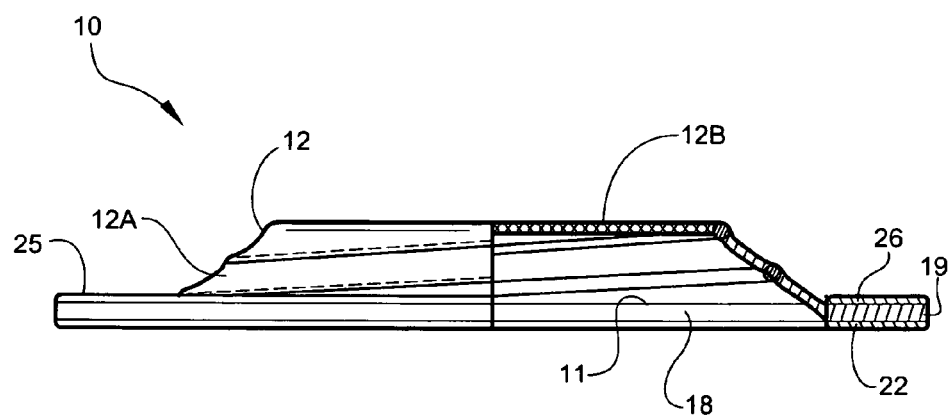
FIG. 5 is a further partial cross-section of the medical dressing with the therapeutic cover in a compressed condition.

The exemplary therapeutic cover 12 has a generally conical shape, and is designed to extend over and above the wound site opening of the annular base 11. The integrally-formed compression spring 14 operates to resiliently and adjustably space the cover 12 from the open wound on the patient. When in a normal extended condition, shown in FIGS. 1, 3, and 4, the cover 12 provides a breathable therapeutic environment intended to promote rapid healing and reduce the risk of infection. In the event a compression force is applied to the medical dressing 10 (e.g., by heavy clothing, weight of the patient, accidental bumping, or the like), the therapeutic cover 12 may adjust to a compressed condition such as that shown in FIG. 5. Once the compression force is removed, the inherent resiliency of the compression spring 14 immediately returns the therapeutic cover 12 to its original extended condition. The compression spring 14 may comprise a helical coil compression spring, although other types of springs and spring-like objects are contemplated herein. Alternatively, the therapeutic cover 12 may be formed of an inherently resilient material, or a material with little or no resiliency (and no compression spring).

Figure 6:
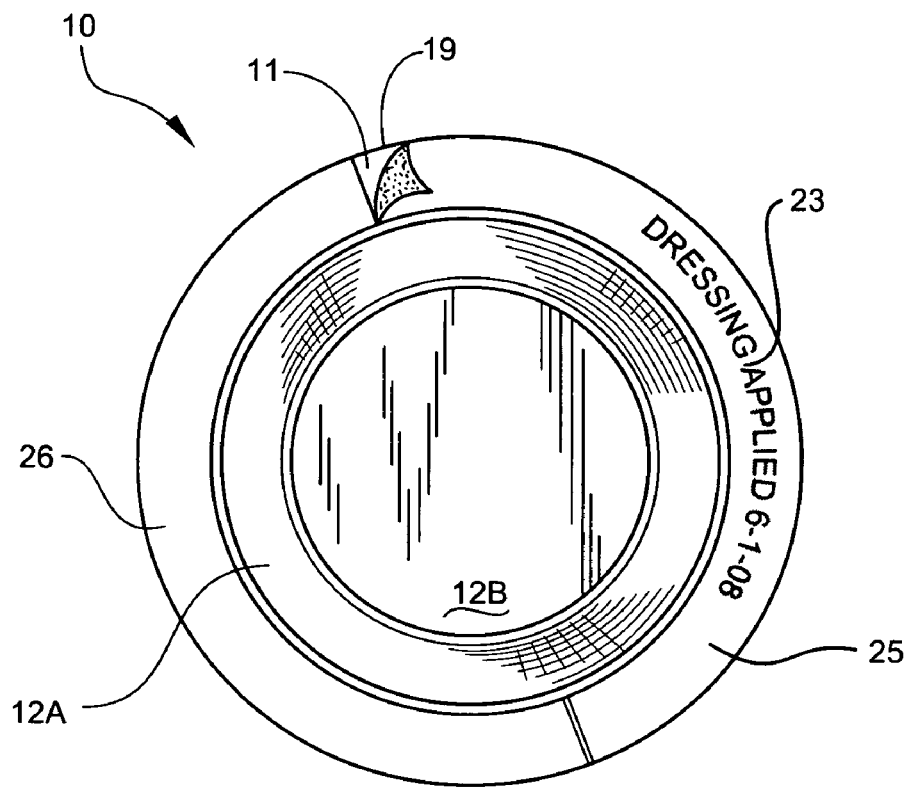
FIG. 6 is a top side view of the medical dressing.

In one exemplary embodiment, the conical side wall 12A of the therapeutic cover 12 is constructed of a thin gauze or gauze-like material comprising loosely woven (meshlike) cotton, while the top wall of the cover forms a substantially see-through wound site window 12B. As best shown in FIG. 6, the wound site window 12B may have a diameter greater than 50% of the annular base 11 diameter, and may be formed of a transparent film or any other suitable material.

Referring again to FIG. 3, the medical dressing 10 may be temporarily adhered to the skin surrounding the open wound using a skin-safe contact adhesive 21 applied to and covering the entire inside major surface 16 of the annular base 11. A poly-coated (e.g., silicone) release paper 22 covers and protects the adhesive 21 prior to application of the medical dressing 10 to the skin. At the time of application, the patient may record his or her name, the date, and any other useful information or indicia 23 (See FIG. 6) on adhesive labels 25 and 26 releasably carried on the outside major surface 17 of the annular base 11. The exemplary labels 25, 26 have a top paper surface, a generally semi-circular shape, and are substantially entirely superimposed upon the annular base 11. The outside major surface 17 of the base 11 may have a poly-coating, such as silicone, between the labels 25, 26 and base 11 to facilitate removal.

Exemplary embodiments of the present invention are described above. No element, act, or instruction used in this description should be construed as important, necessary, critical, or essential to the invention unless explicitly described as such. Although only a view of the exemplary embodiments have been described in detail herein, those skilled in the art will readily appreciate that many modifications are possible in these exemplary embodiments without materially departing from the novel teachings and advantages of this invention. Accordingly, all such modifications are intended to be included within the scope of this invention as defined in the appended claims.

In the claims, any means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. Unless the exact language "means for" (performing a particular function or step) is recited in the claims, a construction under §112, 6th paragraph is not intended. Additionally, it is not intended that the scope of patent protection afforded the present invention be defined by reading into any claim a limitation found herein that does not explicitly appear in the claim itself.

We claim:

1. A medical dressing for an open wound, comprising:
    a base having opposing inside and outside major surfaces, and continuous inside and outside peripheral edges, the inside peripheral, edge defining a wound site opening and designed to surround the open wound;
    an adhesive label releasably adhered to the outside major surface of said base;
    a raised flexible therapeutic cover formed with said base and comprising a perforated flexible gauze, said therapeutic cover extending over and above the wound site opening defined by the inside peripheral edge; and
    means for resiliently spacing said therapeutic cover from the open wound wherein said means comprises a compression spring integrally formed with said therapeutic cover.

2. A medical dressing according to claim 1, wherein said compression spring comprises a helical coil spring.

3. A medical dressing according to claim 1, wherein said therapeutic cover comprises a see-through wound site window.

4. A medical dressing according to claim 3, wherein said wound site window comprises a transparent film.

5. A medical dressing according to claim 1, wherein the outside major surface of said base comprises a silicone coating between said base and said adhesive label.

6. A medical dressing according to claim 1, wherein the inside major surface of said base comprises an adhesive coating adapted for temporarily adhering said medical dressing to skin surrounding the open wound.

7. A medical dressing according to claim 6, and comprising a protective release paper adjacent the adhesive coating of said base.

8. A medical dressing for an open wound, comprising:
- a base comprising an annular flange having opposing inside and outside major surfaces, and continuous inside and outside peripheral edges, the inside peripheral edge defining a wound site opening and designed to encircle the open wound;
- an adhesive label releasably adhered to the outside major surface of said annular flange;
- a raised flexible therapeutic cover formed with said flange and comprising a perforated flexible gauze, said therapeutic cover extending over and above the wound site opening defined by the inside peripheral edge; and
- means for resiliently spacing said therapeutic cover from the open wound wherein said means comprises a compression spring integrally formed with said therapeutic cover.

9. A medical dressing according to claim 8, and comprising first and second substantially semi-circular adhesive labels releasably adhered to the outside major surface of said annular flange.

10. A medical dressing according to claim 8, wherein the outside major surface of said base comprises a silicone coating between said base and said adhesive label.

11. A medical dressing according to claim 8, wherein the inside major surface of said annular flange comprises an adhesive coating adapted for temporarily adhering said medical dressing to skin surrounding the open wound.

12. A medical dressing according to claim 11, and comprising a protective release paper adjacent the adhesive coating of said annular flange.

13. A medical dressing according to claim 8, wherein said means comprises a compression spring integrally formed with said therapeutic cover.

14. A medical dressing according to claim 13, wherein said compression spring comprises a helical coil spring.

15. A medical dressing according to claim 8, wherein said therapeutic cover comprises a see-through wound site window.

16. A medical dressing according to claim 15, wherein said wound site window comprises a transparent film.

17. A medical dressing for an open wound, comprising:
- a base having opposing inside and outside major surfaces, and continuous inside and outside peripheral edges, the inside peripheral edge defining a wound site opening and designed to surround the open wound;
- an adhesive label releasably adhered to the outside major surface of said base;
- a raised flexible therapeutic cover formed with said base and having a top wall at an outermost top of said medical dressing and a bottom located at said base, and said therapeutic cover constructed of a thin fabric material defining a fabric side wall extending from a top side of the top wall to the bottom, and over and above the wound site opening defined by the inside peripheral edge; and
- means for resiliently spacing the top wall of said therapeutic cover from the open wound wherein said means comprises a compression spring integrally formed with said therapeutic cover.

\* \* \* \* \*